United States Patent
Lareau

(10) Patent No.: US 9,132,257 B2
(45) Date of Patent: *Sep. 15, 2015

(54) SELECTIVE SURFACE MODIFICATION OF CATHETER TUBING

(71) Applicant: Boston Scientific Scimed, Inc., Maple Grove, MN (US)

(72) Inventor: Raymond J. Lareau, Westford, MA (US)

(73) Assignee: BOSTON SCIENTIFIC SCIMED, INC., Maple Grove, MN (US)

(*) Notice: Subject to any disclaimer, the term of this patent is extended or adjusted under 35 U.S.C. 154(b) by 0 days.

This patent is subject to a terminal disclaimer.

(21) Appl. No.: 14/316,451

(22) Filed: Jun. 26, 2014

(65) Prior Publication Data

US 2014/0309623 A1  Oct. 16, 2014

Related U.S. Application Data

(63) Continuation of application No. 13/118,111, filed on May 27, 2011, now Pat. No. 8,777,928, which is a continuation of application No. 10/987,010, filed on Nov. 12, 2004, now Pat. No. 7,951,116.

(51) Int. Cl.
*A61M 25/00* (2006.01)
*B29C 47/00* (2006.01)
(Continued)

(52) U.S. Cl.
CPC ....... *A61M 25/0045* (2013.01); *A61M 25/0009* (2013.01); *A61M 25/0054* (2013.01);
(Continued)

(58) Field of Classification Search
CPC ............ A61M 25/0045; A61M 25/0009; A61M 2025/0047; A61M 2025/0046; A61M 2025/0004

USPC ................. 264/176.1; 604/264, 525
See application file for complete search history.

(56) References Cited

U.S. PATENT DOCUMENTS 2,561,569 A  7/1951  Flynn
2,616,126 A  11/1952  Merck et al.
(Continued)

FOREIGN PATENT DOCUMENTS

DE  3917523 A1  12/1990
DE  19651904 A1  6/1998
(Continued)

OTHER PUBLICATIONS

All non-published literature documents and foreign patent documents have been previously uploaded in parent U.S. Appl. No. 13/118,111, filed May 27, 2011 and U.S. Appl. No. 10/987,010, filed Nov. 12, 2004.

(Continued)

*Primary Examiner* — Gerald Landry, II
(74) *Attorney, Agent, or Firm* — Seager, Tufte & Wickhem, LLP

(57) ABSTRACT

A catheter shaft and methods for making and using the same. The catheter shaft may include a core portion, a cap portion, and one or more lumens. The cap portion may be disposed on or over a section of the core portion and define a region with a different exterior or interior surface characteristic. For example, the cap portion may define a lubricious region along the catheter shaft. Manufacturing the catheter shaft may include a modified co-extrusion process that incorporates a flow valve on at least one of the material supply lines so that the supply line can be regulated by a user.

20 Claims, 7 Drawing Sheets

(51) Int. Cl.
*B29C 47/06* (2006.01)
*B29C 47/08* (2006.01)
*B29C 47/26* (2006.01)
*B29C 47/28* (2006.01)
*B29C 47/56* (2006.01)
*B28B 3/20* (2006.01)

(52) U.S. Cl.
CPC ........... *B29C47/0023* (2013.01); *B29C 47/065* (2013.01); *B29C 47/0811* (2013.01); *B29C 47/26* (2013.01); *B29C 47/28* (2013.01); *B29C 47/56* (2013.01); *A61M 2025/006* (2013.01); *A61M 2025/0046* (2013.01); *A61M 2025/0047* (2013.01); *B28B 3/20* (2013.01); *B29C 47/0026* (2013.01); *B29C 47/0028* (2013.01)

(56) References Cited

U.S. PATENT DOCUMENTS

| | | | |
|---|---|---|---|
| 2,940,126 A | 6/1960 | Sheridan | |
| 3,015,355 A | 1/1962 | Humphrey | |
| 3,193,878 A | 7/1965 | Corbett | |
| 3,404,203 A | 10/1968 | Donald | |
| 3,712,782 A | 1/1973 | Burlis | |
| 3,724,985 A | 4/1973 | Burlis et al. | |
| 3,752,617 A | 8/1973 | Burlis et al. | |
| 3,824,479 A | 7/1974 | Alger | |
| 3,891,374 A | 6/1975 | Ninomiya et al. | |
| 3,944,641 A | 3/1976 | Lemelson | |
| 4,005,166 A | 1/1977 | Quick | |
| 4,138,457 A | 2/1979 | Rudd et al. | |
| 4,209,476 A | 6/1980 | Harris | |
| 4,250,072 A | 2/1981 | Flynn | |
| 4,272,466 A | 6/1981 | Harris | |
| 4,276,250 A | 6/1981 | Satchell et al. | |
| 4,277,432 A | 7/1981 | Woinowski | |
| 4,283,447 A | 8/1981 | Flynn et al. | |
| 4,293,294 A | 10/1981 | Rasmussen et al. | |
| 4,330,497 A | 5/1982 | Agdanowski et al. | |
| 4,332,759 A | 6/1982 | Ide | |
| 4,430,282 A | 2/1984 | Stack | |
| 4,430,283 A | 2/1984 | Burnett et al. | |
| 4,430,698 A | 2/1984 | Harris | |
| 4,447,239 A | 5/1984 | Krutten | |
| 4,657,024 A | 4/1987 | Coneys | |
| 4,729,662 A | 3/1988 | O'Brien | |
| 4,734,240 A | 3/1988 | Chung | |
| 4,783,647 A | 11/1988 | Wood | |
| 4,786,181 A | 11/1988 | O'Brian | |
| 4,790,970 A | 12/1988 | Kurth et al. | |
| 4,830,805 A | 5/1989 | Kousai et al. | |
| 4,838,778 A | 6/1989 | Becker et al. | |
| 4,858,139 A | 8/1989 | Wirtz | |
| 4,888,146 A | 12/1989 | Dandeneau | |
| 4,919,605 A | 4/1990 | Kousai et al. | |
| 4,956,143 A | 9/1990 | McFarlane | |
| 4,981,478 A | 1/1991 | Evard et al. | |
| 4,990,143 A | 2/1991 | Sheridan | |
| 5,059,375 A | 10/1991 | Lindsay | |
| 5,063,018 A | 11/1991 | Fontirroche et al. | |
| 5,085,649 A | 2/1992 | Flynn | |
| 5,125,913 A | 6/1992 | Quackenbush | |
| 5,128,077 A | 7/1992 | Stevenson et al. | |
| 5,156,785 A | 10/1992 | Zdrahala | |
| 5,156,857 A | 10/1992 | Wang et al. | |
| 5,215,614 A | 6/1993 | Wijkamp et al. | |
| 5,240,537 A | 8/1993 | Bodicky | |
| 5,248,305 A | 9/1993 | Zdrahala | |
| 5,312,356 A * | 5/1994 | Engelson et al. | 604/164.13 |
| 5,374,245 A | 12/1994 | Mahurkar | |
| 5,409,644 A | 4/1995 | Martin et al. | |
| 5,456,674 A | 10/1995 | Bos et al. | |
| 5,498,377 A | 3/1996 | Ozaki et al. | |
| 5,505,887 A | 4/1996 | Zdrahala et al. | |
| 5,520,870 A | 5/1996 | Allan et al. | |
| 5,531,721 A * | 7/1996 | Pepin et al. | 604/525 |
| 5,533,985 A | 7/1996 | Wang | |
| 5,542,937 A * | 8/1996 | Chee et al. | 604/523 |
| 5,589,236 A | 12/1996 | Harvey et al. | |
| 5,622,665 A | 4/1997 | Wang | |
| 5,639,409 A | 6/1997 | Van Muiden | |
| 5,695,789 A | 12/1997 | Harris | |
| 5,725,814 A | 3/1998 | Harris | |
| 5,734,240 A | 3/1998 | Janca et al. | |
| 5,738,742 A | 4/1998 | Stevens | |
| 5,755,704 A * | 5/1998 | Lunn | 604/527 |
| 5,836,925 A | 11/1998 | Soltesz | |
| 5,843,539 A | 12/1998 | Harvey et al. | |
| 5,851,477 A | 12/1998 | Halgren et al. | |
| 5,868,718 A | 2/1999 | Pepin et al. | |
| 5,882,741 A | 3/1999 | Rubin et al. | |
| 5,947,940 A | 9/1999 | Beisel | |
| 5,951,494 A | 9/1999 | Wang et al. | |
| 5,968,438 A | 10/1999 | Imaizumi | |
| 5,984,657 A | 11/1999 | Bentivoglio | |
| 6,030,369 A | 2/2000 | Engelson et al. | |
| 6,048,484 A | 4/2000 | House et al. | |
| 6,103,037 A | 8/2000 | Wilson | |
| 6,135,992 A | 10/2000 | Wang | |
| 6,165,166 A | 12/2000 | Samuelson et al. | |
| 6,171,295 B1 | 1/2001 | Garabedian et al. | |
| 6,280,423 B1 | 8/2001 | Davey et al. | |
| 6,319,228 B1 * | 11/2001 | Kastenhofer | 604/96.01 |
| 6,436,056 B1 | 8/2002 | Wang et al. | |
| 6,458,069 B1 | 10/2002 | Tam et al. | |
| 6,530,765 B1 | 3/2003 | Zdrahala et al. | |
| 6,663,614 B1 | 12/2003 | Carter | |
| 6,776,945 B2 | 8/2004 | Chin et al. | |
| 7,163,523 B2 * | 1/2007 | Devens et al. | 604/96.01 |
| 7,662,144 B2 | 2/2010 | Chan et al. | |
| 2002/0119264 A1 | 8/2002 | Wang | |
| 2003/0009151 A1 | 1/2003 | Wang | |
| 2003/0030165 A1 | 2/2003 | Centell et al. | |
| 2004/0064130 A1 | 4/2004 | Carter | |
| 2004/0210211 A1 | 10/2004 | Devens, Jr. et al. | |
| 2004/0243102 A1 | 12/2004 | Berg et al. | |
| 2005/0115624 A1 * | 6/2005 | Walak | 138/139 |
| 2005/0124976 A1 * | 6/2005 | Devens et al. | 604/523 |
| 2006/0051535 A1 | 3/2006 | Arney et al. | |
| 2006/0106351 A1 * | 5/2006 | Lareau | 604/264 |

FOREIGN PATENT DOCUMENTS

| | | |
|---|---|---|
| EP | 0417865 A1 | 3/1991 |
| EP | 0437291 A1 | 7/1991 |
| EP | 0528181 A1 | 2/1993 |
| EP | 0618059 A1 | 10/1994 |
| EP | 0662385 A1 | 7/1995 |
| EP | 0992335 A2 | 4/2000 |
| JP | 6015004 A | 1/1994 |
| JP | 9309139 A | 12/1997 |
| JP | 2001309533 A | 11/2001 |
| WO | 9325372 A1 | 12/1993 |
| WO | 9524304 A1 | 9/1995 |
| WO | 9529051 A1 | 11/1995 |
| WO | 9600100 A1 | 1/1996 |
| WO | 9626671 A1 | 9/1996 |
| WO | 9626825 A1 | 9/1996 |
| WO | 9736629 A1 | 10/1997 |
| WO | 0001420 A2 | 1/2000 |

OTHER PUBLICATIONS

Lusignea, R., "Flexible Multilayer Packaging with Oriented LCP Barrier Layer," TAPPI Proceedings, (1998) pp. 889-899.

* cited by examiner

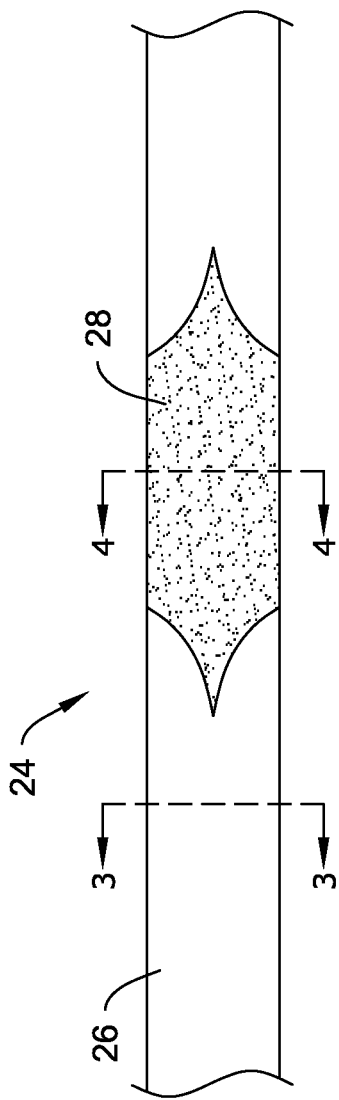
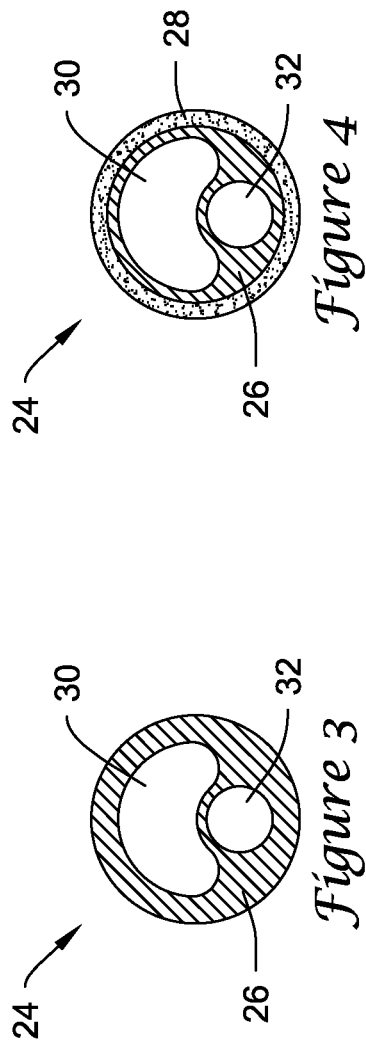

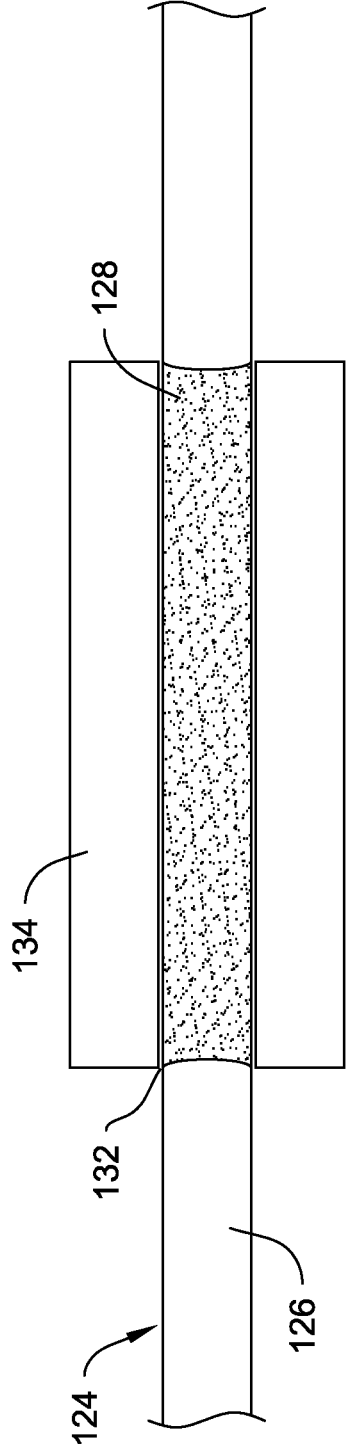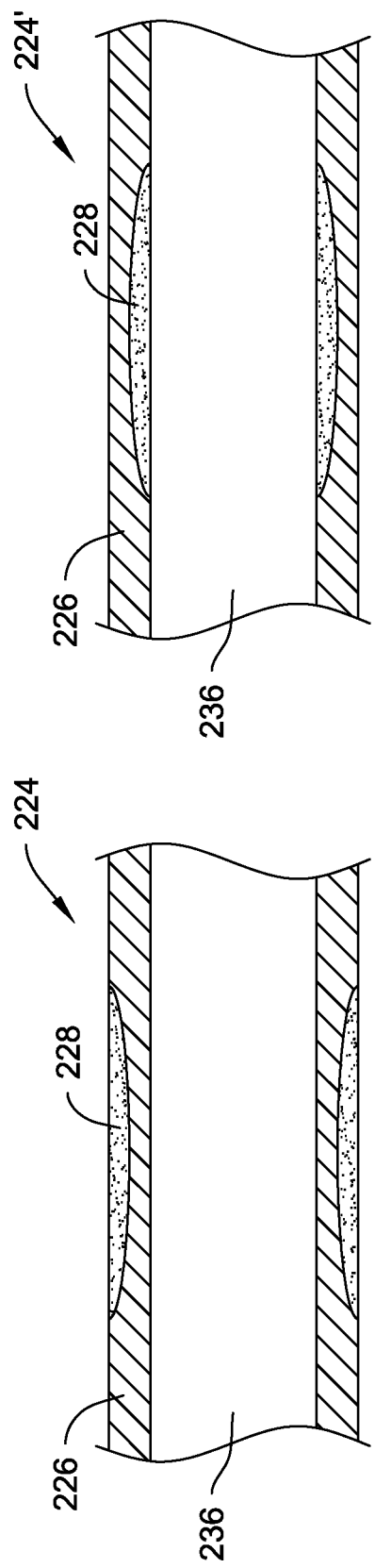

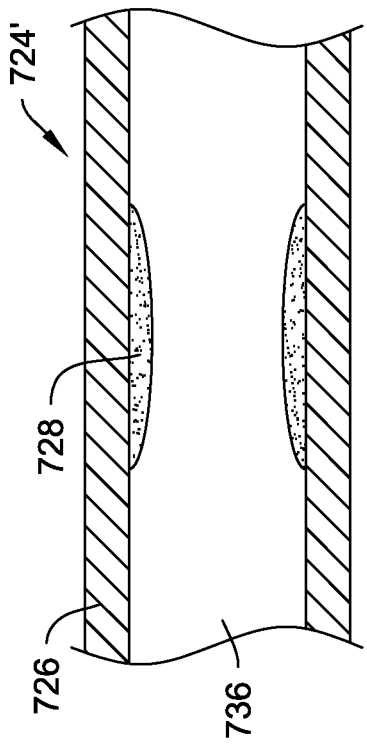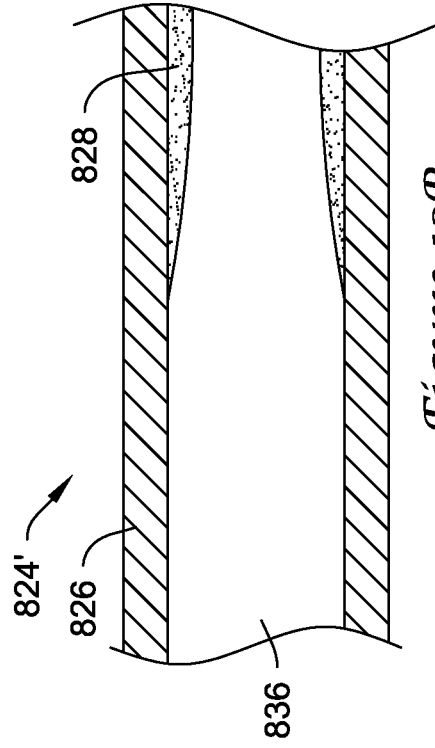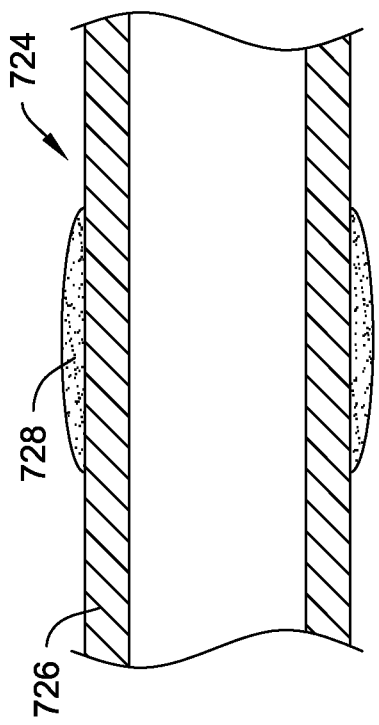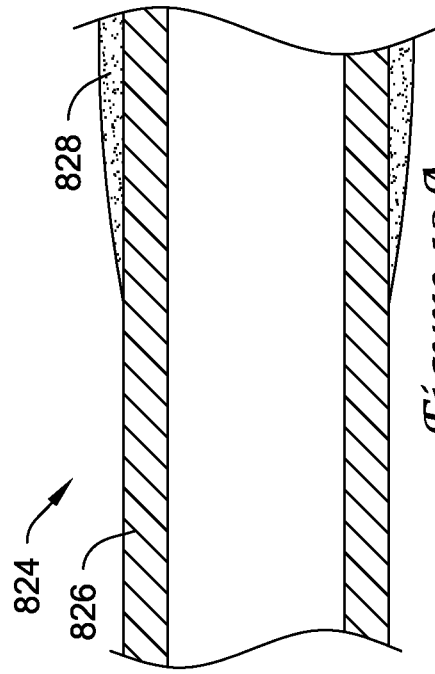
Figure 11A
Figure 11B
Figure 12A
Figure 12B

SELECTIVE SURFACE MODIFICATION OF CATHETER TUBING

RELATED APPLICATIONS

This application is a continuation of co-pending U.S. application Ser. No. 13/118,111, filed May 27, 2011, which is a continuation of U.S. application Ser. No. 10/987,010, filed Nov. 12, 2004, now U.S. Pat. No. 7,951,116, the entire disclosures of which are incorporated herein by reference.

FIELD OF THE INVENTION

The present invention pertains to medical devices and methods for making and using medical devices. More particularly, the present invention pertains to catheter shafts with surface modifications and/or changes in surface characteristics as well as methods for making catheter shafts with surface modifications.

BACKGROUND

A wide variety of medical devices have been developed. At least some of these devices are designed to pass through an opening or lumen in the body or through a lumen or channel (e.g., a working channel) in another medical device. For example, the device may comprise a catheter (e.g., therapeutic, diagnostic, or guide catheter), an endoscopic device, a laproscopic device, an embolic protection device, and the like, or any other suitable device. Among these known devices, each has certain advantages and disadvantages. There is an ongoing need to provide alternative designs and methods of making and using new and improved medical devices.

BRIEF SUMMARY

The invention provides design, material, and manufacturing method alternatives for catheters, catheter shafts, and the like. In at least some embodiments, a catheter shaft may include a generally tubular catheter shaft. The catheter shaft may include a core portion, a cap portion, and one or more lumens defined therein. The cap portion may be disposed on or over a section of the core portion and define a region with a different exterior or interior surface characteristic. For example, the cap portion may define a lubricious region along the catheter shaft. Some of the other features of this catheter shaft and others like it are described in more detail below.

Manufacturing the catheter shaft may include a modified co-extrusion process. The modified process incorporates a flow valve on at least one of the material supply lines so that the supply line can be regulated by a user. For example, a user may vary the amount of material from an extruder to be used in the production of the catheter shaft anywhere between 0-100% of the total output. This allows the catheter shaft to be manufactured with different characteristics (e.g., surface characteristics) without the need for additional coating, fusing, or attachment steps. Some other features of this method and other methods like it are described in more detail below.

The above summary of some embodiments is not intended to describe each disclosed embodiment or every implementation of the present invention. The Figures, and Detailed Description which follow, more particularly exemplify these embodiments.

BRIEF DESCRIPTION OF THE DRAWINGS

The invention may be more completely understood in consideration of the following detailed description of various embodiments of the invention in connection with the accompanying drawings, in which:

FIG. 2 is a side view of an example catheter shaft;

FIG. 3 is a cross-sectional view of a portion of the catheter shaft shown in FIG. 2;

FIG. 4 is a cross-sectional view of another portion of the catheter shaft shown in FIG. 2;

FIG. 5 is a partial cross-sectional side view of an example catheter shaft disposed in the working channel of an endoscope;

FIG. 6A is a cross-sectional side view of another example catheter shaft;

FIG. 6B is a cross-sectional side view of another example catheter shaft;

FIG. 11A is a cross-sectional side view of another example catheter shaft;

FIG. 11B is a cross-sectional side view of another example catheter shaft;

FIG. 12A is a cross-sectional side view of another example catheter shaft; and FIG. 12B is a cross-sectional side view of another example catheter shaft.

DETAILED DESCRIPTION

Figure 1:
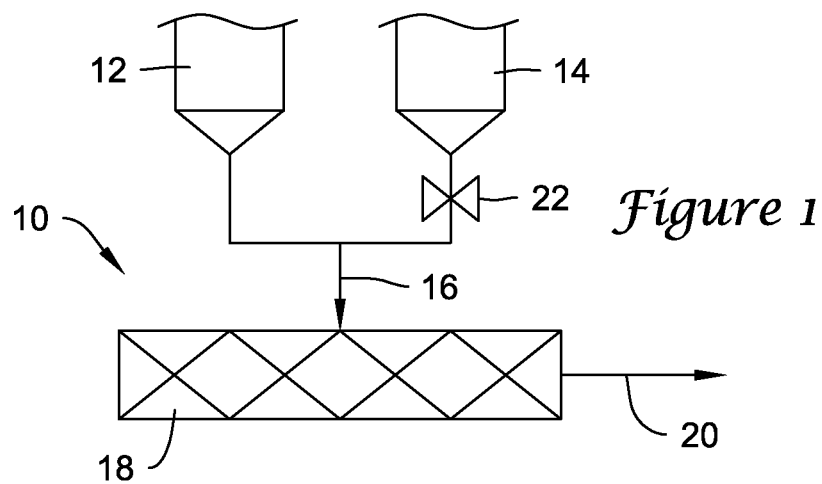
FIG. 1 is a schematic overview depicting an example co-extrusion apparatus.

The following description should be read with reference to the drawings wherein like reference numerals indicate like elements throughout the several views. The detailed description and drawings illustrate example embodiments of the claimed invention.

FIG. 1 is a schematic view of an example extrusion apparatus 10 that may be used to manufacture a catheter, catheter shaft, or other similar medical device. Apparatus 10 may include a first feed hopper or reservoir 12 and a second feed hopper or reservoir 14. In at least some embodiments, the two feed hoppers 12/14 may combine at a feed pipe or cross-head 16 and feed an extruder 18. The output of extruder 18 is indicated by reference number 20. Feed hoppers 12/14 may hold different manufacturing materials so that the modified co-extrusion process can produce a multi-layered or multi-material device such as shaft 24 as best seen in FIG. 2. In some embodiments, additional feed hoppers or extruders may be included that hold and supply additional materials. Output 20 may be any suitable medical device (or a precursor thereto) such as a catheter (e.g., angioplasty, stent delivery, therapeutic, diagnostic, or guide catheter) or catheter shaft, an endoscopic device, a laproscopic device, an embolic protection device, or any other suitable device.

Apparatus 10 differs from other co-extrusion devices in that it includes a flow valve 22 coupled thereto. In at least some embodiments, flow valve 22 is positioned so that it can regulate the flow of material from feed hopper 14. Of course, flow valve 22 could alternatively be used to regulate feed hopper 12 (and/or any other feed hopper that may be present) or an additional flow valve 22 can be used to regulate feed hopper 12 in concert with the valve 22 regulating the flow from feed hopper 14. Flow valve 22 can be configured so that it can meter the flow from feed hopper 14 so that the supply of material from feed hopper 14 can be completely stopped (i.e., 0% flow), completely open or continuously flowing (i.e., 100% flow), or anywhere in between. In at least some embodiments, at least one material (e.g. the material from feed hopper 12) constantly feeds cross-head 16 while the other material (e.g., the material from feed hopper 14) is regulated as described above. Accordingly, apparatus 10 allows, for example, output 20 to constantly include one material (e.g., the material supplied by feed hopper 12) and include a variable amount of a second material (e.g., the material supplied by feed hopper 14 and regulated by valve 22). This includes the ability to apply material from feed hopper 14 to multiple, discrete sections of the resultant device.

Valve 22 may be similar to other typical valves. For example, valve 22 may be a simple on/off diverting valve or something more complicated like a computer programmed proportional shut off valve. Either way, valve 22 may utilize a pneumatic, hydraulic, or other standard transfer means for controlling flow. In some embodiments, valve 22 diverts material within or away from extruder 18. Alternatively, valve 22 may be part of a closed extrusion system that creates a "compression chamber" where materials are contained and reused. In general, valve 22 may be adjusted between a number of positions. For example, valve 22 may have a first configuration or setting that substantially blocks the flow of material from second hopper 14 to extruder 18 and a second configuration that allows the material in second hopper 14 to flow to extruder 18. A number of additional settings or configurations may also exist that alter the amount of material that is permitted to flow from second hopper 14 to extruder 18.

This modified co-extrusion process may be desirable for a number of reasons. For example, because the supply from feed hopper 14 is regulated by valve 22 for the cap portion of a shaft (not shown in FIGS. 1 and 1A, please see, for example, cap portion 28 in FIG. 2), there is less waste than in other intermittent co-extrusions where larger volumes of materials are displaced from the extruder and become waste. This savings of material can be significant, especially if higher cost materials are used, such as polymers doped with radiopaque fillers (including precious metals). Another desirable feature may be that a single process can be used to manufacture a product having a variable material composition. In fact, apparatus 10 allows for the combination of extruding and so-called "coating" or "capping" steps. For example, feed hopper 12 may be used to supply the "core" material and feed hopper 14 may be used to coat or cap the core. In addition, output 20 may produce complex products including multi-lumen tubing that is coated internally or externally. This may be desirable because the process reduces any trepidation regarding the possibility of melting the tube, thereby collapsing any or all of the lumens, during a potentially heat-intensive subsequent coating and/or sleeving operation. This feature may also be advantageous when it is desirable to coat one or more portions of the core, for example, to impart a desired surface characteristic to a selective portion or portions of a device. Other desirable features may include an improved interface between shaft 24 sections due to the fact that fusing or bonding individual sections is no longer required, fewer method steps to produce a finished product (no need to connect tube section via adhesive bonding, thermal bonding, welding, and the like), increased strength at the interface between shaft sections because of the continuous and seamless transition between sections, etc.

It should be noted that at least some embodiments utilize flow valve 22 for only one of the two illustrated hoppers 12/14. Accordingly, using flow valve 22 to completely stop the flow from feed hopper 14 would result in output 20 coming from feed hopper 12. Similarly, using flow valve 22 open 100% would result in output 20 comprising a combination of the materials from feed hopper 12 and hopper 14. The proportions of materials coming from hopper 12 and hopper 14 can vary depending on the set up of apparatus 10 and the setting of valve 22. This embodiment is also distinct from other co-extrusion devices where only a constant flow of multiple materials or a transition from 100% of a first material to 100% of a second material (abruptly or gradually) is possible.

Figure 1A:
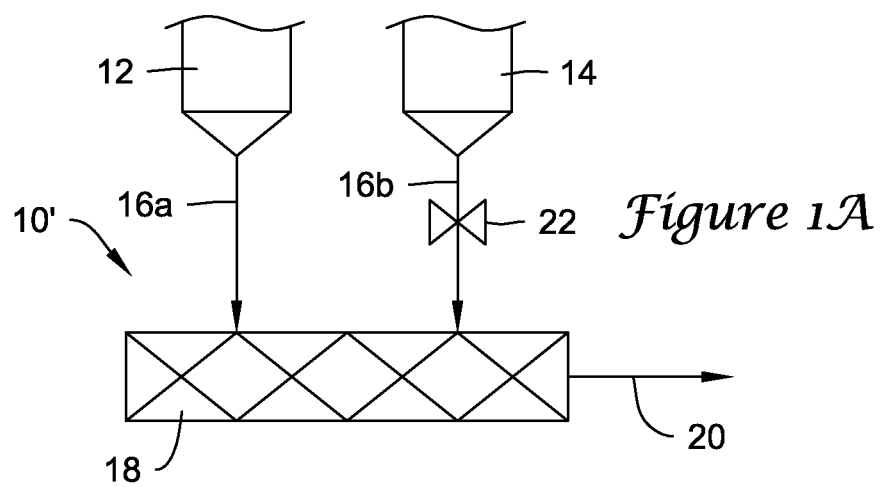
FIG. 1A is a schematic overview depicting another example co-extrusion apparatus.

Apparatus 10 depicts the flow of materials from hoppers 12/14 (including the metered control from hopper 14) into a common cross-head 16. This need not be the only suitable arrangement, because other flow patterns are contemplated. For example, FIG. 1A is a schematic view of another example extrusion apparatus 10'. Apparatus 10' is similar to apparatus 10 except that first hopper 12 and second hopper 14 feed into their own individual feed pipes 16*a/b* and flow valve 22 regulate flow in feed pipe 16*b*. This drawing indicates that the modified co-extrusion process that is disclosed herein can also vary in the way materials loaded in feed hoppers 12/14 are delivered to extruder 18. A number of additional variations in the setup of apparatus 10' (and apparatus 10) are contemplated and are thought to be well within the spirit and scope of the invention.

Figure 1B:
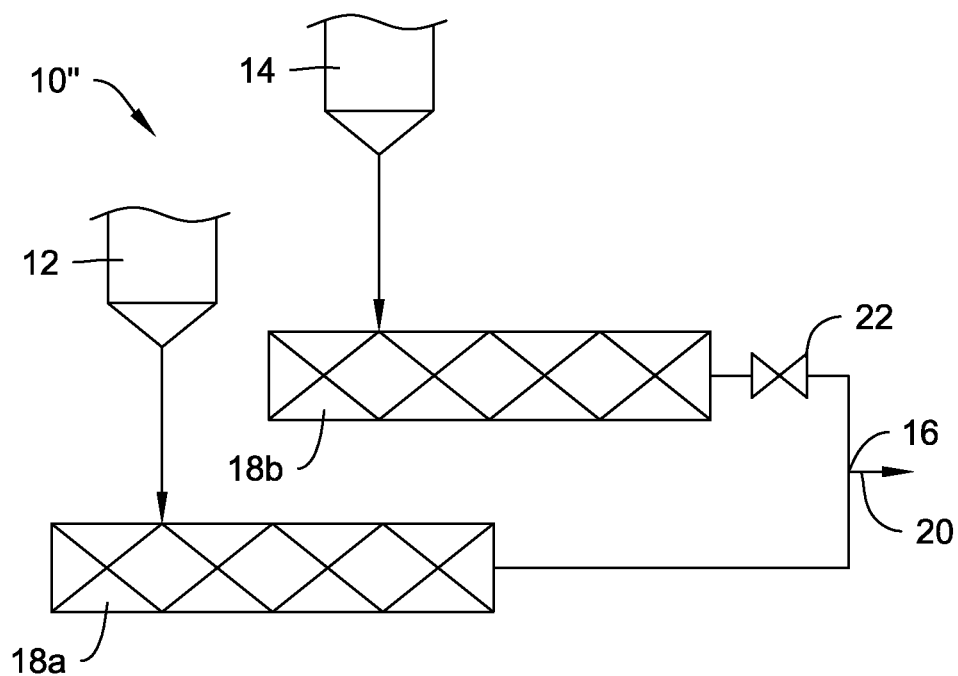
FIG. 1B is a schematic overview depicting another example co-extrusion apparatus.

FIG. 1B is a schematic view of another example extrusion apparatus 10". Apparatus 10" is similar to apparatus 10/10' except that first hopper 12 and second hopper 14 are each coupled to their own extruders (i.e., extruders 18*a* and 18*b*, respectively), and then extruders 18*a*/18*b* feed into a common cross-head 16. Flow valve 22 regulates the flow of material from one of the extruders (e.g., extruder 18*b*) into the common cross-head. Of course, flow valve 22 could just as easily regulate the flow from extruder 18*a* or a second flow valve 22 may be utilized so that the flow can be regulated from both extruder 18*a* and 18*b*. This drawing indicates that the modified co-extrusion process that is disclosed herein can also vary in the way materials from a plurality of sources (e.g., extruders 18*a*/18*b*) are delivered to a common cross-head 16. Output 20 from apparatus 10", therefore, includes material from feed hopper 12 and extruder 18*a* and a regulated amount of material from feed hopper 12 and extruder 18*b*, depending on the extent to which valve 22 is open or closed. A number of additional variations in the setup of apparatus 10" (and apparatus 10 and 10') are contemplated and are thought to be well within the spirit and scope of the invention. For example, additional feed hoppers and extruders may be added that can also feed into cross-head 16 or be arranged in parallel to cross-head 16.

FIG. 2 is a side view of an example catheter shaft 24 that may be manufactured using apparatus 10, apparatus 10', or any of the contemplated variations of these devices. Shaft 24 may include a core portion 26 and a cap portion 28. In at least some embodiments, core portion 26 is manufactured by extrusion of the materials supplied from feed hopper 12 or another "unregulated" or "unvalved" hopper or extruder. Cap portion 28 can be manufactured by regulated co-extrusion of the materials supplied from hopper 14 or another hopper or extruder that includes valve 22. Thus, manufacturing of shaft 24 can include an extrusion similar to what is described above where valve 22 is used to specify the desired location(s) and lengths for cap portion 28. The embodiment shown depicts that cap portion 28 can be positioned at a centralized location of shaft 24 (i.e., away from the ends of shaft 24). Thus, some regions of shaft 24 may include only core portion 26, as best seen in cross-section at FIG. 3, and other regions of shaft 24 may include core portion 26 capped with cap portion 28, as best seen in cross-section at FIG. 4.

The materials used to manufacture shaft 24 can vary considerably. For example, core portion 26 and cap portion 28 may be each made from a polymer such as a thermoplastic (including neat and filled thermoplastic resins). Some examples of suitable polymers may include thermoplastic urethane elastomers, polyurethane, polyamide (for example, DURETHAN® available from Bayer or CRISTAMID® available from Elf Atochem), elastomeric polyamides, polyether block amide (PEBA, for example, available under the trade name PEBAX®), ethylene vinyl acetate copolymers (EVA), polyethylene (PE) including linear low, low, medium, and high density polyethylene, polyethylene terephthalate (PET), other suitable materials, or mixtures, combinations, copolymers thereof, polymer/metal composites, and the like.

Generally, the materials selected for core portion 26 are selected based on their flexibility characteristics (such as being sufficiently stiff) or other physical characteristics that are desirable for the intended application of shaft 24. The materials selected for cap portion 26 may be selected so as to impart a change in the exterior or interior surface of shaft 24. For example, the materials selected for cap portion 28 may define a region of shaft 24 that has a high hardness or is lubricious. In addition, because of the flow regulation achievable through the use of valve 22, the desired surface characteristic (for example, lubricity) can be positioned only where (and/or every place) it is needed or desired. Lubricious coatings improve steerability and improve the ability of shaft 24 to pass through or otherwise be moveable within another device such as the working channel of an endoscope. Thus, the addition of cap portion 28 may define a region on shaft 24 that is optimized for tracking in a working channel of an endoscope. In addition, the addition of cap portion 28 internally may define a region optimized for deploying coils or for guidewire tracking. Another desirable application for cap portion 28 may be defining a region along shaft 24 that is configured for attaching an angioplasty balloon or another object. Suitable lubricious polymers are well known in the art and may include silicone co-polymers and the like, hydrophilic polymers, high-density polyethylene (HDPE), polytetrafluoroethylene (PTFE), fluoropolymers, polyarylene oxides, polyvinylpyrolidones, polyvinylalcohols, hydroxy alkyl cellulosics, algins, saccharides, caprolactones, and the like, and mixtures and combinations thereof. Any of these materials, any other material disclosed herein, or any other suitable material may be used to manufacture cap portion 28.

Even though it is disclosed above that cap portion 28 may be a lubricious material (and that core portion 26 may be a generally non-lubricious material or another material), this is not intended to be limiting. For example, in some embodiments, core portion 26 may include a lubricious material and cap portion 28 may be "non-lubricious".

A number of alternative surface characteristics and other modifications may be incorporated into shaft 24 via cap portion 28. For example, cap portion 28 may be made from a material that provides increased chemical and/or thermal resistance, changes in hardness, adds radiopacity, increases or decreases MRI compatibility, or the like. For example, cap portion 28 may include a polymer doped with gold, platinum, palladium, tantalum, tungsten alloy, or another radiopaque material so as to define a surface with increased radiopacity. In at least some embodiments, cap portion 28 may be configured to elute or otherwise deliver a pharmaceutical agent. For example, cap portion 28 may include a slow-release form of a drug (such as an anti-clotting drug, for example) that can help reduce clotting that might otherwise occur without the drug. Of course, this structure and use is not intended to be limiting to anti-clotting drugs as any drug may be substituted without departing from the spirit of the invention.

The aforementioned apparatuses 10/10' and the illustrated shaft 24 describe how devices can be produced with discrete sections having a selectively modified surface. Thus, a portion of the exterior or interior of shaft 24 is defined by core portion 26, and another portion of the exterior or interior of shaft 24 is defined by cap portion 28. The relevant exterior or interior portions can have different surface characteristics. This feature may be desirable for a number of applications. For example, endoscopic retrograde cholangiopancreatography (ERCP) techniques utilize an endoscope where it is desirable to use a catheter shaft that has a lubricious exterior section suitable for being disposed in the working channel of the endoscope and a less lubricious or "tacky" distal tip with a lower hardness that is suitable for cannulation of the major duodenal papilla or for probing sphincters and other body orifices. In addition, cap portion 28 may also modify the flexibility of shaft 24 and, in some embodiments, act as a strain relief.

As stated above, shaft 24 can be a catheter shaft or another type or component of a medical device. Accordingly, shaft 24 may include a number of additional features. For example, shaft 24 may have one or more lumens defined therein such as a first lumen 30 and a second lumen 32 as best seen in FIGS. 3 and 4. First lumen 30 may be used, for example, to infuse contrast media, pharmaceuticals, angioplasty balloon inflation media, and the like, or any other suitable material. Second lumen 32 may be used, for example, as a guidewire lumen. A number of additional uses for lumens 30/32 are contemplated.

FIGS. 3 and 4 also illustrate another feature of shaft 24. By comparing FIG. 3 with FIG. 4 it can be seen that both sections have essentially the same outer diameter (e.g., in the range of about 0.02 to about 0.35 inches or so). This is because extruder 18 can be configured to produce shaft 24 having a variable composition while maintaining a constant outer diameter by coupling with a variable speed take-off unit. For example, extruder 18 may be configured so that as the amount of material from hopper 14 (i.e., the hopper that cap portion 28 is made from) that reaches the cross-head 16 (or the extrusion die) increases, the amount of material making up shaft 24 from hopper 12 (i.e., the hopper that core portion 26 is made from) proportionally decreases. This allows a constant outer diameter shaft 24 to be produced that may also have a constant wall thickness. However, this need not be the particular arrangement. For example, other embodiments of shaft 24 may include one or more tapers as is commonly seen in the catheter art or that include changes in wall thickness.

Shaft 24 may also include a number of additional structural features commonly associated with catheters and similar medical devices. For example, shaft 24 could include an angioplasty balloon, and embolic protection filter, a stent and/or means for expanding or retrieving a stent, a radiopaque marker, etc. Moreover, shaft 24 may include additional sections or components coupled thereto including metallic or polymeric shafts. These other metallic components may include metals typically used in catheters such as nickel-titanium alloy, stainless steel, etc.

FIG. 5 illustrates an example catheter shaft 124 disposed in the working channel 132 of an endoscope 134. This Figure illustrates the usefulness of cap portion 128 for use with endoscopes such as endoscope 134. FIG. 5 depicts that cap portion 128 has a different exterior surface characteristic (i.e., lubricity) than core portion 126. This arrangement allows shaft 124 to be easily manipulated when disposed within working channel 132.

FIGS. 6A-12B depict various shafts that include differing arrangements of cap and core portions. Each embodiment may include any of the features described above for similarly named or depicted structures. For example, FIG. 6A illustrates shaft 224 having core portion 226 and a discrete cap portion 228 disposed away from the ends of shaft 224 much like shaft 24 as depicted in FIG. 2. The one or more lumens that can be present in shaft 224 are shown in FIG. 6 as a singular lumen 236. However, lumen 236 is shown in this manner for the purpose of simplification. It can be appreciated that shaft 224 could also be generally solid (i.e., without lumen 236) or include more than one lumen. FIG. 6B depicts shaft 224', which is similar to shaft 224 except that cap portion 228 is disposed along the interior surface (i.e., adjacent lumen 236) of shaft 224'.

Figure 7A:
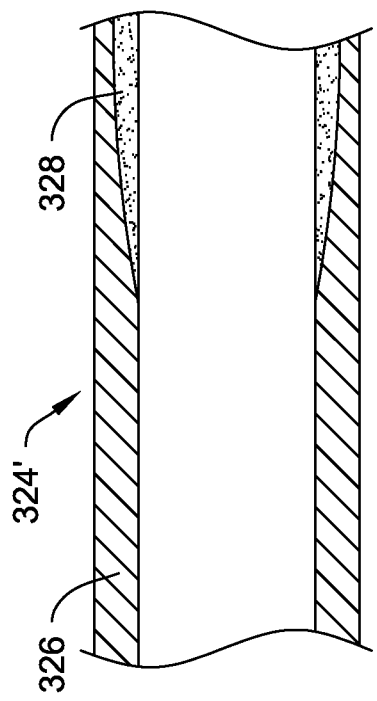
FIG. 7A is a cross-sectional side view of another example catheter shaft.
Figure 7B:
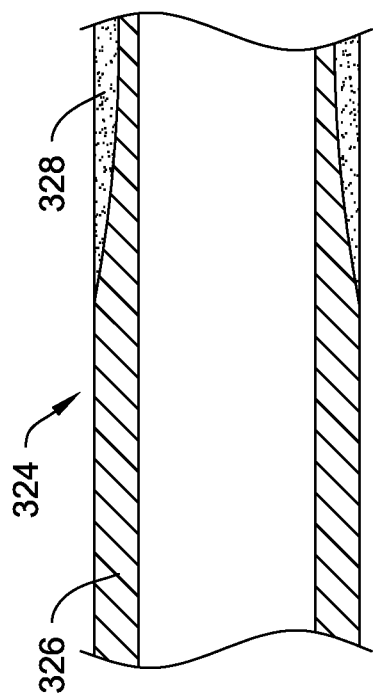
FIG. 7B is a cross-sectional side view of another example catheter shaft.

FIG. 7A is another example shaft 324 that includes core portion 326 and cap portion 328. According to this embodiment, cap portion 328 may begin at some centralized location (i.e., not at the end) and extend toward the end of shaft 324. In some embodiments, cap portion 328 may extend all the way to one end of shaft 324. In some other embodiments, cap portion 328 can extend all the way across shaft 324 to both ends. FIG. 7B depicts shaft 324', which is similar to shaft 324 except that cap portion 328 is disposed along the interior surface (i.e., adjacent lumen 336) of shaft 324'.

Figure 8A:
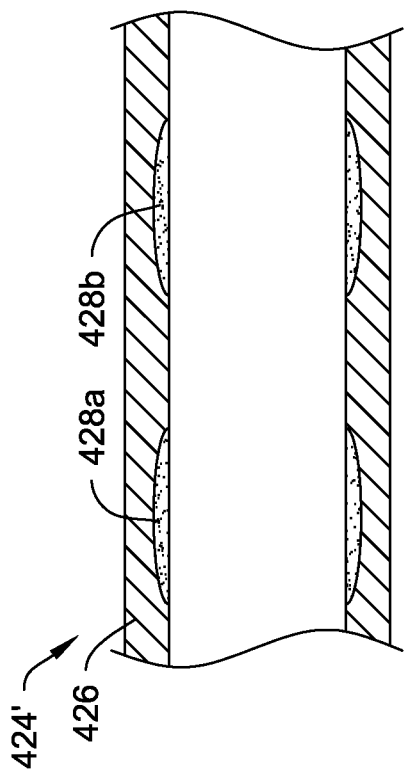
FIG. 8A is a cross-sectional side view of another example catheter shaft.
Figure 8B:
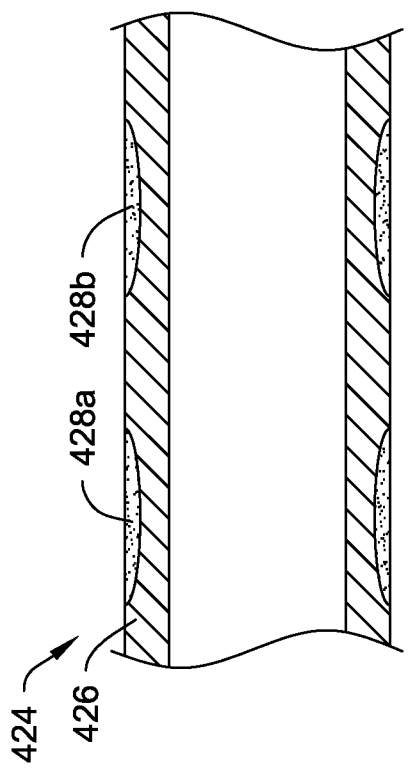
FIG. 8B is a cross-sectional side view of another example catheter shaft.

FIG. 8A is another example shaft 424 that includes core portion 426 and multiple cap portions 428a/b. This embodiment illustrates that multiple cap portions 428a/b may be utilized for shaft 424 or any of the shafts disclosed herein. FIG. 8B depicts shaft 424', which is similar to shaft 424 except that cap portions 428a/b are disposed along the interior surface of shaft 424'.

Figure 9A:
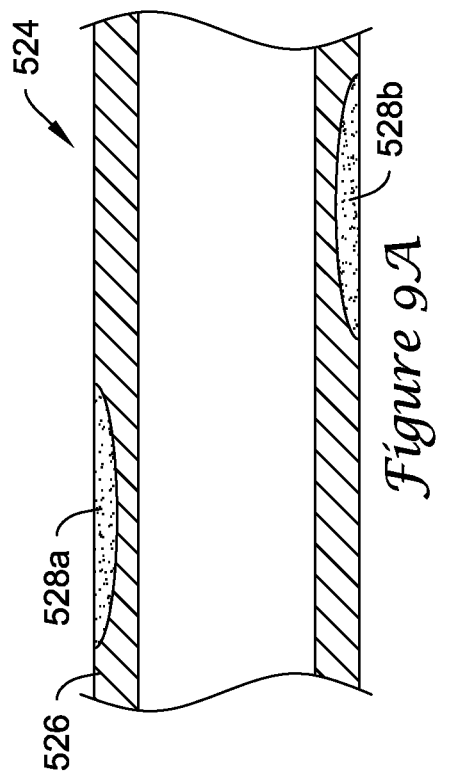
FIG. 9A is a cross-sectional side view of another example catheter shaft.
Figure 9B:
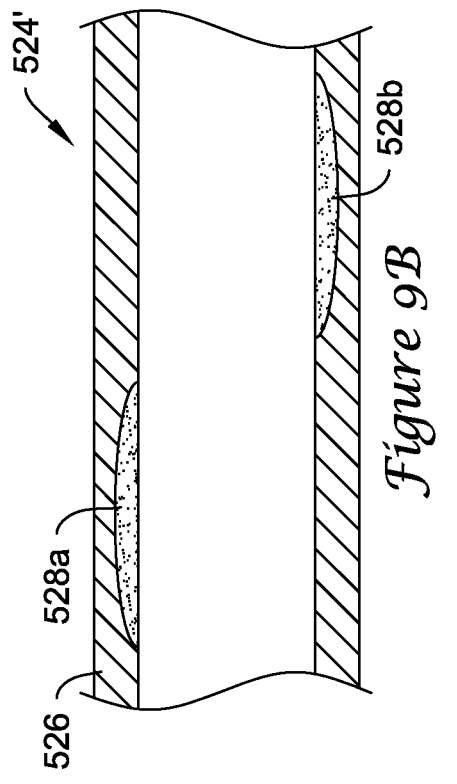
FIG. 9B is a cross-sectional side view of another example catheter shaft.

Similarly, FIG. 9A illustrates shaft 524 where the different cap portions 528a/b are spatially limited to a particular section of cap portion 526. This later feature can be achieved, for example, by adding further control to the radial position to which cap portion 528 is disposed on. FIG. 9B depicts shaft 524', which is similar to shaft 524 except that cap portions 528a/b are disposed along the interior surface of shaft 524'.

Figure 10A:
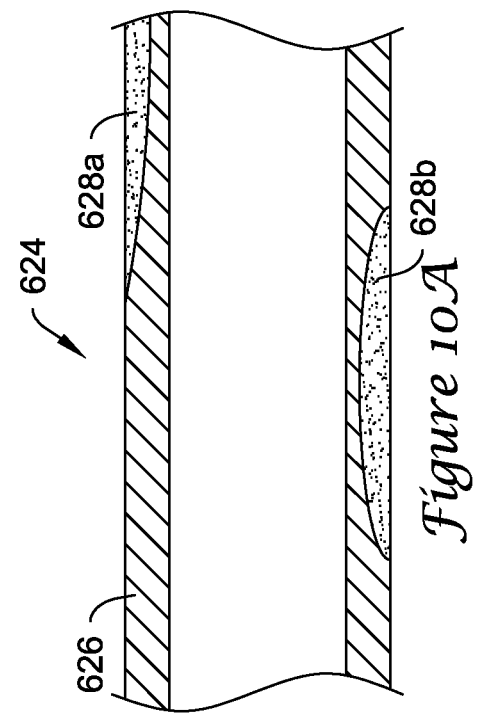
FIG. 10A is a cross-sectional side view of another example catheter shaft.
Figure 10B:
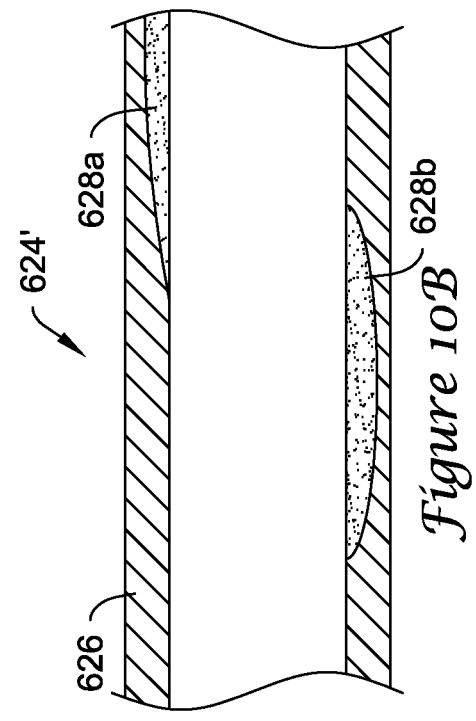
FIG. 10B is a cross-sectional side view of another example catheter shaft.

FIG. 10A similarly shows shaft 624 where cap portion 628a is radially limited to one section of core portion 626 (and extends therefrom toward the end of shaft 624) whereas cap portion 628b is radially limited to another more centralized section of core portion 626. FIG. 10B depicts shaft 624', which is similar to shaft 624 except that cap portions 628a/b are disposed along the interior surface of shaft 624'.

FIG. 11A illustrates another example shaft 724 including core portion 726 and cap portion 728. Here it can be seen that cap portion 728 may be coated or otherwise added onto a generally constant core portion 726. Accordingly, cap portion 728 appears "raised" or otherwise projects outward from the exterior of core portion 726. FIG. 11B depicts shaft 724', which is similar to shaft 724 except that cap portion 728 is disposed along the interior surface of shaft 724' and extend into lumen 736.

Additionally, shaft 824, depicted in FIG. 12A, may include core portion 826 and a similarly configured cap portion 828. Cap portion 828 may be raised along the exterior of core portion 826 and extend toward at least one of the ends of shaft 824. FIG. 12B depicts shaft 824', which is similar to shaft 824 except that cap portion 828 is disposed along the interior surface of shaft 824' and extend into lumen 836.

It should be understood that this disclosure is, in many respects, only illustrative. Changes may be made in details, particularly in matters of shape, size, and arrangement of steps without exceeding the scope of the invention. The invention's scope is, of course, defined in the language in which the appended claims are expressed.

What is claimed is:

1. A catheter shaft, comprising:
   a catheter shaft comprising a first portion, a second portion, and a third portion, the catheter shaft having a constant outer diameter;
   wherein the second portion is positioned between the first portion and the third portion;
   wherein the first portion includes a first material;
   wherein the second portion includes a first layer of the first material disposed over a second layer of a second material such that the second layer of the second material defines an inner surface of the catheter shaft;
   wherein the first material has a first surface characteristic and the second material has a second surface characteristic different from the first surface characteristic; and
   wherein the first surface characteristic is more lubricious than the second surface characteristic.

2. The catheter shaft of claim 1, wherein the first surface characteristic is harder than the second surface characteristic.

3. The catheter shaft of claim 1, wherein the second surface characteristic is harder than the first surface characteristic.

4. The catheter shaft of claim 1, wherein the second material defines a first cap portion along the second portion of the catheter shaft.

5. The catheter shaft of claim 4, wherein the second portion includes a second cap portion longitudinally spaced from the first cap portion.

6. The catheter shaft of claim 4, wherein the first cap extends into a lumen of the catheter shaft.

7. The catheter shaft of claim 1, wherein the first material defines a first layer disposed about an entire outer circumference of catheter shaft.

8. The catheter shaft of claim 1, wherein the first material defines a first layer extending about only a portion of an outer circumference of the catheter shaft.

9. The catheter shaft of claim 1, wherein the third portion includes the first material and is free of the second material.

10. The catheter shaft of claim 1, wherein the catheter shaft comprises at least one lumen defined therein.

11. A medical device, comprising:
    a catheter shaft having a first portion and a second portion;
    wherein the first portion and the second portion are seamlessly connected and have the same outer diameter;
    wherein the first portion includes a first material;

wherein the second portion includes a first layer of the first material and a second layer of a second material;

wherein the first material has a first surface characteristic and the second material has a second surface characteristic different from the first surface characteristic; and wherein the first material is more lubricious than the second material.

12. The medical device of claim 11, wherein the first layer of the first material defines an inner surface of the catheter shaft and the second layer of second material is disposed over the first layer of the first material.

13. The medical device of claim 11, wherein the first layer of the first material defines an exterior surface of the catheter shaft and is disposed over the second layer of the second material, wherein the second layer of the second material defines an inner surface of the catheter shaft.

14. The medical device of claim 11, wherein the second layer of the second material is disposed over the first layer of the first material and extends about the entire circumference of the catheter shaft.

15. The medical device of claim 11, wherein the second layer of the second material is disposed over the first layer of the first material and extends about only a portion of the catheter shaft.

16. The medical device of claim 11, wherein the second layer of the second material comprises two or more discrete segments, the two or more discrete segments including a first segment longitudinally space apart from a second segment along the catheter shaft.

17. The medical device of claim 16, wherein the second layer of the second material is disposed over the first layer of the first material, wherein the first layer of the first material defines an inner surface of the catheter shaft.

18. A medical device, comprising:

a catheter shaft having a first portion and a second portion;

wherein the first portion and the second portion are seamlessly connected and have a constant wall thickness;

wherein the first portion includes a first material;

wherein the second portion includes a first layer of the first material and a second layer of a second material;

wherein the first material has a first surface characteristic and the second material has a second surface characteristic different from the first surface characteristic; and wherein the first layer is more lubricious than the second material layer.

19. The medical device of claim 18, wherein the first layer of the first material defines an exterior surface of the catheter shaft and is disposed over the second layer of the second material, wherein the second layer of the second material defines an inner surface of the catheter shaft.

20. The medical device of claim 18, wherein the first portion and the second portion have a same outer diameter.

* * * * *